US009801757B2

(12) United States Patent
Voss et al.

(10) Patent No.: US 9,801,757 B2
(45) Date of Patent: Oct. 31, 2017

(54) LIQUID DISPENSING RESERVOIR

(75) Inventors: Leslie A. Voss, Jacksonville, FL (US);
Gary S. Hall, Jacksonville, FL (US);
Catie A. Morley, St. Johns, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 9 days.

(21) Appl. No.: 13/600,105

(22) Filed: Aug. 30, 2012

(65) Prior Publication Data

US 2013/0172831 A1 Jul. 4, 2013

Related U.S. Application Data

(60) Provisional application No. 61/529,627, filed on Aug. 31, 2011.

(51) Int. Cl.
| | |
|---|---|
| *A61M 11/00* | (2006.01) |
| *A61M 5/142* | (2006.01) |
| *A61F 9/00* | (2006.01) |
| *B05B 9/04* | (2006.01) |
| *B05B 9/08* | (2006.01) |
| *B05B 11/00* | (2006.01) |

(52) U.S. Cl.
CPC .............. *A61F 9/00* (2013.01); *A61F 9/0008* (2013.01); *A61M 11/00* (2013.01); *A61M 11/005* (2013.01); *A61M 11/008* (2014.02); *B05B 9/042* (2013.01); *B05B 9/0861* (2013.01); *B05B 9/0872* (2013.01); *A61M 2205/3569* (2013.01); *A61M 2205/3592* (2013.01); *A61M 2205/8206* (2013.01); *A61M 2205/8231* (2013.01); *B05B 11/30* (2013.01)

(58) Field of Classification Search
CPC .................. A61M 11/00; A61M 5/142; A61M 2005/14208; A61M 5/14232; A61M 5/14244; A61M 37/0092; A61M 5/14228
See application file for complete search history.

(56) References Cited

U.S. PATENT DOCUMENTS

| | | | | |
|---|---|---|---|---|
| 6,495,015 | B1 * | 12/2002 | Schoeniger et al. | 204/600 |
| 2002/0107492 | A1 * | 8/2002 | Brach | B65D 35/28 604/296 |
| 2003/0106902 | A1 * | 6/2003 | Bolam | 222/92 |
| 2005/0247558 | A1 * | 11/2005 | Anex et al. | 204/275.1 |
| 2007/0066955 | A1 * | 3/2007 | Sparholt et al. | 604/415 |
| 2008/0113130 | A1 * | 5/2008 | Schell et al. | 428/34.8 |
| 2008/0173545 | A1 * | 7/2008 | Anex et al. | 204/600 |
| 2009/0036844 | A1 * | 2/2009 | Fristrup | A61J 1/1406 604/288.04 |
| 2011/0152913 | A1 * | 6/2011 | Jones et al. | 606/192 |

* cited by examiner

*Primary Examiner* — Kari Rodriquez
*Assistant Examiner* — Sara Sass

(57) ABSTRACT

This invention provides for a device and methods of dispensing a precise predetermined volume of liquid of discrete drops, vapor, or mist while preventing contamination due to Pull Back and ensuring precision dispensing.

22 Claims, 4 Drawing Sheets

LIQUID DISPENSING RESERVOIR

CROSS REFERENCE TO RELATED APPLICATIONS

This application claims priority to Provisional U.S. provisional Patent Application Ser. No. 61/529,627 filed on Aug. 31, 2011 and entitled "Liquid Dispensing Reservoir" the contents of which are relied upon and incorporated herein by reference.

FIELD OF USE

This invention describes a device for dispensing precise quantities of liquids in a discrete drop(s), vapor, or mists, and more specifically, a reservoir capable of providing uncontaminated liquids due to its capability to eliminate any significant Pull Back and/or additional fluid expelling pressure forces resulting from elastomeric properties of the material of the reservoir used and the liquid dispensed.

BACKGROUND OF THE INVENTION

Liquid containers have been known and used to dispense liquids for various applications in the medical field. Although most are effective for their basic purpose, an improved container to dispense small volumes of liquids is desired for some applications. For example, liquid containers are used to dispense a liquid or a mist into an eye using many different devices. However, although many devices result with a liquid entering the eye, the experience of getting the liquid into the eye is generally less than satisfactory.

Devices for self-dispensing liquids into the eye typically require that a user hold the eyelids open to fight the blink reflex. This contention inhibits easy an application of the desired fluids. Some automated devices pull down on one lid, or encapsulate the eye area to stop the lids from closing. This touch is damaging to makeup, and can lead to contamination of the device and the liquid entering the eye.

The dose from the system should consistently, without great user effort, dispense into the user's eye, not upon the eyelid or other part of the users face, and optimally should not touch the face in a manner that damages makeup or contaminates the device.

Some dispensing devices simulate a 'gun' and shoot a fluid in at the eye at a rate calculated to beat the blink reflex, however the speed and impact of the fluid seem to induce significant discomfort to the patient.

Other devices force the lids open in different manners through touching the cheek below the lid, and the eyebrow range above the upper lid, then spray the fluid into the eye. This forcing open of the lids is uncomfortable, and the unit itself becomes large and unwieldy. Any makeup worn by the consumer is smudged during the process and sometimes contaminates the dispenser and/or the dispensed liquid.

Misting of fluid over the entire eye or even the facial area is also feasible, but doing so wets not only the eye, but undesirable surfaces such as the eyelid, forehead, and nose. Application of liquid to the eyelid is declared to also wet the eye by flowing into the eye, but results from this method are mixed, and the wetting of the lid itself is typically undesirable.

SUMMARY OF THE INVENTION

Accordingly, the present invention includes a reservoir suitable for the administration of small volumes of fluids, wherein the reservoir is capable of eliminating any significant Pull Back from the liquid dispensed and/or additional fluid expelling pressure forces caused by stiffness/elastomeric properties of a material used. By eliminating the Pull Back and additional fluid expelling pressure forces that result in conventional systems, the reservoir can be used in applications where the volume of liquid dispensed is trivial and contamination prevention is desired. As a result, the reservoir may be used in conjunction with an array of medical devices eliminating current restrictions in the present systems/devices. For example, the reservoir will be useful for spraying a liquid, such as a drug, vitamin or lubricant into an Ophthalmic Environment.

DETAILED DESCRIPTION OF THE INVENTION

Figures 1A, 1B:
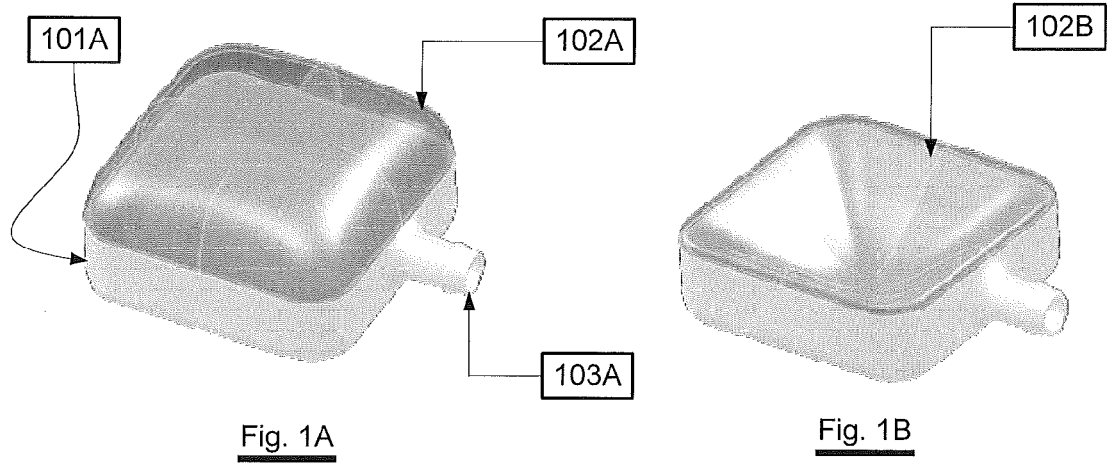
FIGS. 1A, 1B and 1C illustrate an exemplary reservoir that may be used as part of a liquid dispensing device according to some embodiments of the present invention.

The present invention provides for a device used for small volume liquid dispensing in precise predetermined quantities with contamination prevention functionality. In the following sections detailed descriptions of embodiments of the invention will be given. The description of both preferred and alternative embodiments though thorough are exemplary embodiments only, and it is understood that to those skilled in the art that variations, modifications, and alterations may be apparent. It is therefore to be understood that the exemplary embodiments do not limit the broadness of the aspects of the underlying invention as defined by the claims.

Glossary

In this description and claims directed to the presented invention, various terms may be used for which the following definitions will apply:

"Dispensing Tip" as used herein, refers to a valve, pump, or similar device, which dispenses liquid from a liquid path to an exterior environment.

"Highly Sensitive Flexible Foil" as used herein, refers to a thin flexible portion of the reservoir and can include a foil capable of responding to the pressure differential caused by a lost volume as low as 0.4 micro liters. For example, it can include a medical grade CRYOVAC® M312A film, RAHMEDIC™ PE-14 or STERIPAK™ COC film which are PENTAMED™ PETG suitable thin materials with a thickness of approximately 0.005-0.4 mm.

"Jet Dispensing" as used herein and sometimes referred to "Dispensing", refers to a non-contact administration process that utilizes a fluid jet to shoot and form droplets of liquid from the Dispensing Tip.

"Ophthalmic Environment" as used herein, refers to the Dispensing area that includes Dispensing onto a surface of an eye or into an area protected by an eyelid.

"Peristaltic Pump" as used herein, refers to a non-contaminating pump where fluid only contacts the tubing—rollers of a motor-driven pump head push a precise amount of the fluid along the tubing as they rotate.

"Pump" as used herein, refers to a device that transfers liquid from a reservoir to the Dispensing Tip by a pumping action. Pumps may be driven with motors, solenoids or air pressure and may be included inside the reservoir.

"Pull Back" as used herein, refers to the decompression or pull-back due to a pressure difference. For example, in most conventional medical grade vented containers, the pressure difference created when dispensing a liquid from the container would result in Pull Back.

"Valve" as used herein, refers to a device that controls or regulates the flow of material from a reservoir, to the dispensing tip by opening and closing a passageway. For example, a passive valve.

"Viscosity" as used herein, refers to the measure of a liquid's resistance to deformation under mechanical stress. Viscosity is a function of fluid temperature and usually decreases as temperature increases.

"Voids (entrapped air)" as used herein, refers to air bubbles due to Pull Back in the vessel, reservoir, or feed channels to the dispensing tip that may cause inaccuracies of quantities dispensed and contamination of the liquid.

Different liquid containers have been used in the field of liquid packaging. In the medical field, suitable liquid containers must comply with medical grade requirements. Compliance with these requirements is important for volume accuracy, contamination prevention, and reliability in its intended use. To provide a liquid container that complies with medical grade requirements, the volume of container, material, configuration, and sterilization and filling capabilities are all important design parameters. This invention takes into account these design parameters and provides a novel liquid container, more specifically, the liquid container being a self-collapsible medical grade liquid reservoir suitable for small volumes of liquids.

Referring now to FIG. 1A, an exemplary self-collapsing reservoir that may be used as part of a liquid dispensing device according to some embodiments of the present invention is depicted at its filled state. At 102A, a flexible foil is shown. The flexible foil 102A can be capable of acting as a lid and be leak tight sealed to a rigid portion 101A of the reservoir to prevent diffusion of gases and liquids. The leak tight seal may be performed by one or more of the many methods of sealing medical grade containers. However, the flexible foil must be capable of responding (i.e. collapse) to pressure differential created by dispensing liquid volumes as small as 0.5 micro liters in some medical applications, for example, when used by the ophthalmic fluid dispensing device described in other parts of this invention. As such, the flexible foil part of the reservoir must be highly responsive to small pressure differences to avoid any substantial Pull Back that could cause air particles to be sucked into the liquid fluid path thereby exposing them to the medical grade fluid to be used for future doses, i.e. susceptible to possible contamination, and also prevent any substantial additional fluid expelling pressure forces resulting from elastomeric properties of the material used and the liquid dispensed. A highly responsive medical grade flexible foil, as required in some embodiments, may include Cryovac M312A film, Rahmedic PE-14 or Steripak COC film which are Pentamed PETG suitable thin materials with a thickness of approximately 0.03-0.4 mm. In other embodiments where medical grade requirements are not present, other flexible films may be used, for example, a sandwich layer of polyethylene terephthalate (PET), aluminum (Al) and polyethylene (PE) with a thickness of 12/9/75 µm respectively, having the PE layer of the foil in contact with the liquid in the reservoir. Additionally, the Aluminum layer may be included in either to serve for purposes of diffusion and UV barrier in some embodiments where protection of the liquid from UV light is desired. Referring now to FIG. 1B, the exemplary self-collapsing reservoir depicted in FIG. 1A is shown after the flexible foil 102A collapsed from liquid dispensing.

Referring back to FIG. 1A, at 101A, the rigid portion of the reservoir to which the top flexible foil is sealed to is depicted. The rigid portion can also be of medical grade, capable of containing medical aqueous solutions as required for some embodiments. Moreover, where medical aqueous solutions are to be dispensed, all of the components of the reservoir in direct contact with the solution must allow proper sterilization. The rigid portion is an essential part of the reservoir in some embodiments, whether the dispensed liquid is of medical grade or not, for three reasons. First, by having a rigid portion allows an increase of the sensitivity of the flexible foil, so that it can collapse when very small volumes of the liquid are dispensed. For example, in the eye liquid dispensing device described in other parts of this invention, for volumes extracted as small as 0.5 to 20 micro liters, from a reservoir with liquid capacities of 1 to 4 milliliters in some embodiments. However, in other embodiments and depending on the application, the volume can be greater as it is only dependent on the drop administration regimen prescribed and the desired shelf life of the medical fluid. Second, it can provide airless filling capabilities for the reservoir. Airless filling capabilities may be achieved to prevent Voids when dispensing the liquid when the accuracy of the volume dispensed is trivial to the application. Airless filling essentially provides a reservoir where any substantial amount of air that would contaminate or cause Voids when dispensing is pushed out. A way of achieving this can be by pushing the flexible foil into the rigid portion during the welding process, to thereafter fill the reservoir with the liquid to be dispensed. (In some embodiments, the process may further require a vacuum unit to take any remaining air out before filling and sealing a port as further described hereafter.) Lastly, the rigid portion of the reservoir can accommodate at least one port made out of the same material as the reservoir or, for example, isoprene—a natural rigid rubber available in medical grade if so required. This port can be part of a fluid path or connected to a fluid path connected to a Dispensing Head for liquid dispensing and as further described in the proceeding figures.

Figure 1C:
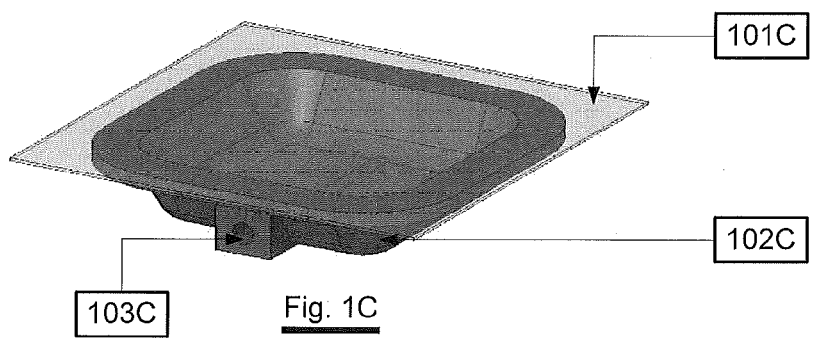

Referring now to FIG. 1C, a model of yet another exemplary reservoir that may be used as part of a liquid dispensing device according to some embodiments of the present invention is depicted. This configuration was tested to make sure the flexible foil 101C would bend in and out of the rigid portion 102C corresponding to the liquid content of the reservoir, eliminating any significant Pull Back. Different volumes of liquid and different aluminum foils were tested to ensure the limitations of the conventional reservoir bags were eliminated and it was acceptable for small volumes of liquids. During the experiment, the same rigid portion 102C and port 103C were used using a suitable droplet generator device (not shown). Three different samples of Flexible foil were used. Sample C included CRYOVAC® M312 with a foil thickness of 0.2 mm; Sample R included RAHMEDIC™ PE-140 with a foil thickness of 0.15 mm and Sample S which included STERIPAK™ COC with a thickness of 0.175 mm. Pull Back, different volumes, Viscosity of the liquid, and performance were all analyzed to conclude that it a suitable flexible foil could be selected depending on any of these factors without undue experimentation. For example, it was determined that the softer and thinner the foil is, the better performance of the flexible foil when using smaller volumes of fluid, 0.25 ml-2 ml reservoir. Further, it was observed during testing of Sample R with a smaller volume of fluid that a few wrinkles were formed when passing the half-filled state. However, the wrinkles did vanish nearly completely in full and empty state, thereby not creating any substantial Pull Back from the dispensing. Other samples, were tested and it was determined they could also be suitable for larger volume of liquid. It was additionally realized that the adherence of the flexible foil to the rigid portion can vary depending on the foil used. To eliminate this problem clamping frames were designed to keep the flexible foil adhered to the rigid portion.

Figure 1D:
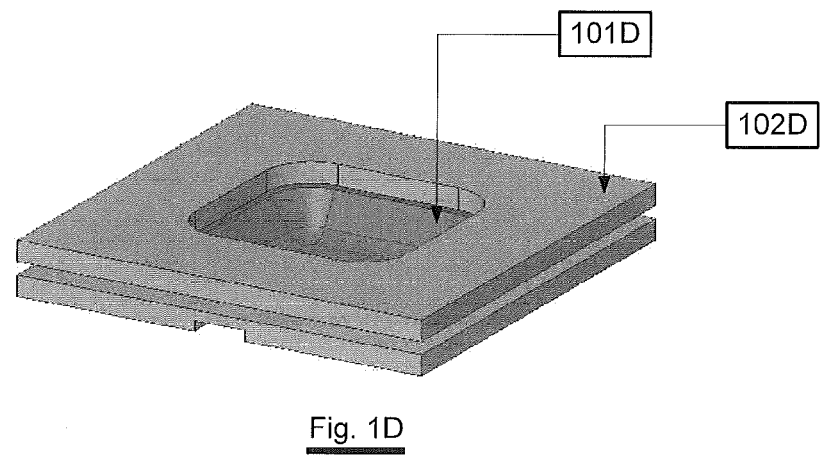
FIG. 1D illustrates the exemplary reservoir in FIG. 1C with a clamp mechanism used to adhere the rigid portion of the reservoir with the flexible foil portion.

Referring now to FIG. 1D, the exemplary reservoir in FIG. 1C with a clamp mechanism used to adhere the rigid portion of the reservoir with the flexible foil portion is depicted. By using clamping frames 102D, it was found that the flexible foil 101D could be pressed down onto a broad edge of the rigid portion thereby providing a leak tight reservoir allowing the flexible foils to bulge in and out undisturbed.

Figure 2:
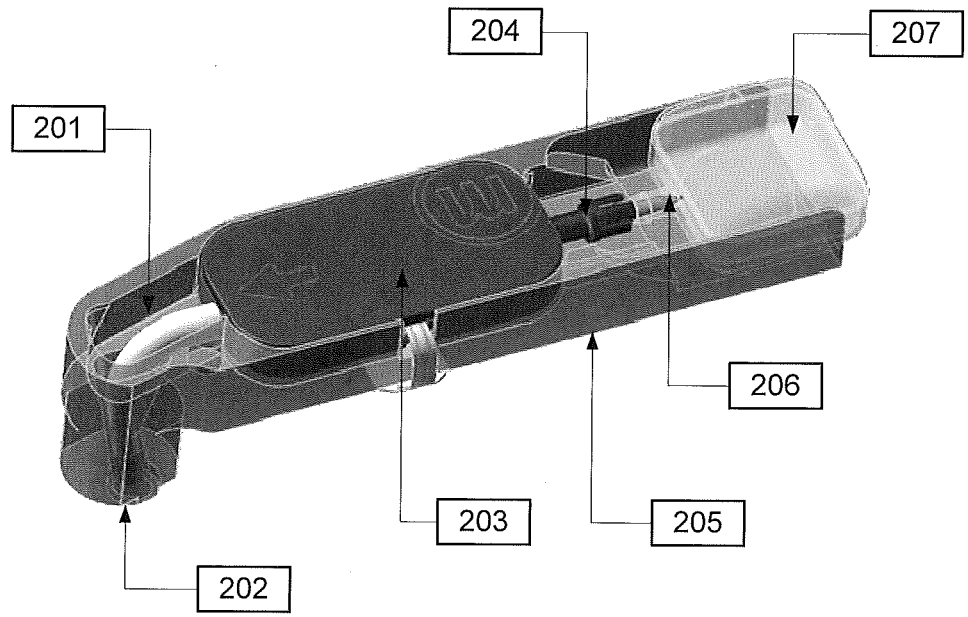
FIG. 2 illustrates an exemplary liquid dispensing device where the liquid fluid path of the reservoir includes a pump.

Referring now to FIG. 2, an exemplary liquid dispensing device where the liquid fluid path of the reservoir can include a pump is depicted. This exemplary embodiment can incorporate the reservoir from this invention, to provide precise, uncontaminated, small volume liquid dispensing to an eye. The parts described in this embodiment are not limiting to the invention but rather are described to provide the reader with an exemplary application and to further convey the how the invention eliminates current limitations in the design of liquid dispensing devices. At 201, the shell of the liquid dispensing device is depicted. The shell of the apparatus should be designed to fix the components of the device, and in applications such as this one, to facilitate use and restrict the user from accessing any non-disposable components to ensure reliability of the device and to prevent contamination of the liquid. Disposable or interchangeable components may include the reservoir and/or batteries used to power the device.

At 202, the Dispensing Head is depicted. The Dispensing Head can vary depending on the application and can be directly connected to the liquid fluid path of the device. In this exemplary embodiment, the Dispensing Head can be one that is capable of Jet Dispensing with the use of a Pump and a microcontroller. At 203, an internal shell is depicted comprising a microcontroller, a Pump, and the fluid path. Other components may include memory, a processor, one or more Valves, and any other known components known in the art. This second internal shell may be used when the liquid dispensed is a medical fluid and the pump used requires the fluid to contact it then making the pump component a disposable part to avoid any contamination to other medical fluids dispensed by the device. However, any of these components may also be placed outside the second internal shell in other embodiments. At 204, a point of connection is depicted, as it may be required when allowing a user to replace the reservoir is desirous. The user may replace the reservoir through an access through an access point 207 on the outer shell of the device. When this is desired, the sealed reservoir can provide the liquid once an adaptor 206 encounters the port of the reservoir thereby connecting it to the liquid fluid path of the device. The adaptor can comprise a perforating part, such as a needle type puncturing tip and/or a Valve since the reservoir can include a pierceable portion of the flexible membrane, for example, a septum that can be lanced by the "adaptor". In some embodiments, the septum must form a leak free seal around the adaptor and must be comprised of materials with less than a 0.2-micron mesh that can act as a barrier against microorganisms. At 205, a means to control the liquid dispensing device can be placed anywhere where it can be convenient for the user in the outer shell of the device. For example, in this case a push button (not shown) may be used in the outer shell portion of the device, which is shaped to allow the user to grip the body and use as a handle.

Figure 3:
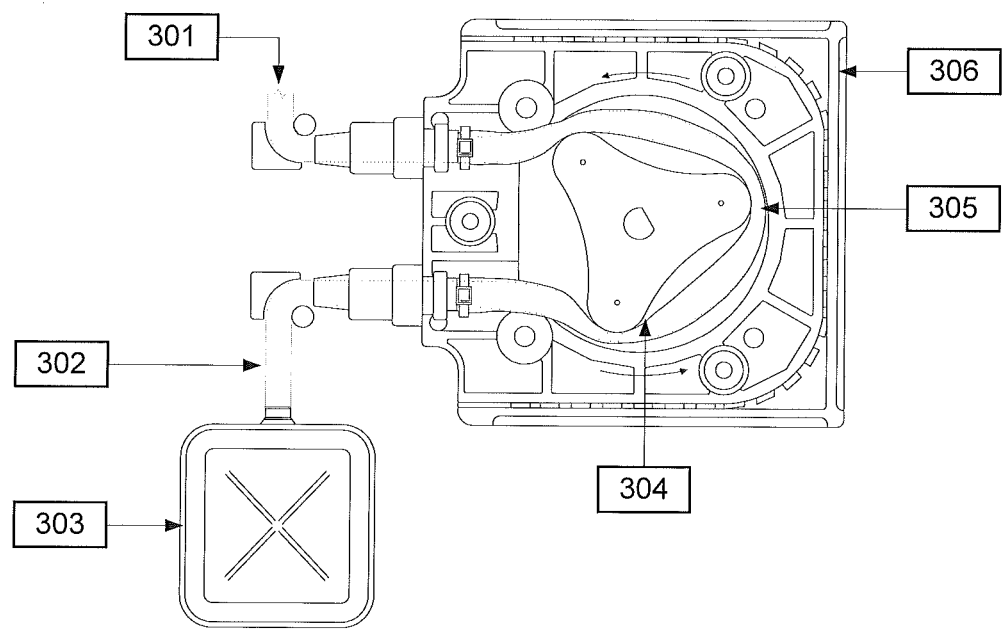
FIG. 3 illustrates an exemplary liquid dispensing Peristaltic pump used to prevent the pump from being part of the liquid fluid path in the liquid dispensing device.

Referring now to FIG. 3, an exemplary liquid dispensing Peristaltic Pump used to prevent the pump from being part of the liquid fluid path in the liquid dispensing device is depicted. By using a Peristaltic Pump, in some embodiments it can be possible to make a disposable piece comprising the reservoir 303, a liquid fluid path and the Dispensing Tip. This can be disposable allowing the replacement of the piece containing another type of liquid, since the liquid being dispensed does not come into contact with the pump thereby contaminating any other liquids later dispensed. At 303, the reservoir is shown with its port attached to a medical grade tubing 302. The medical grade tubing 302 of the reservoir can then be inserted into a second cylindrical path 305 that is flexible to allow the controlled Peristaltic Pump 306 to pressurize the medical grade tubing as predetermined to cause a precise dispensing of the fluid. At 301, an outlet of the medical tubing is provided for the Dispensing Tip at the opposite end of the reservoir in the liquid fluid path to become fixed with the external shell.

Figure 4:
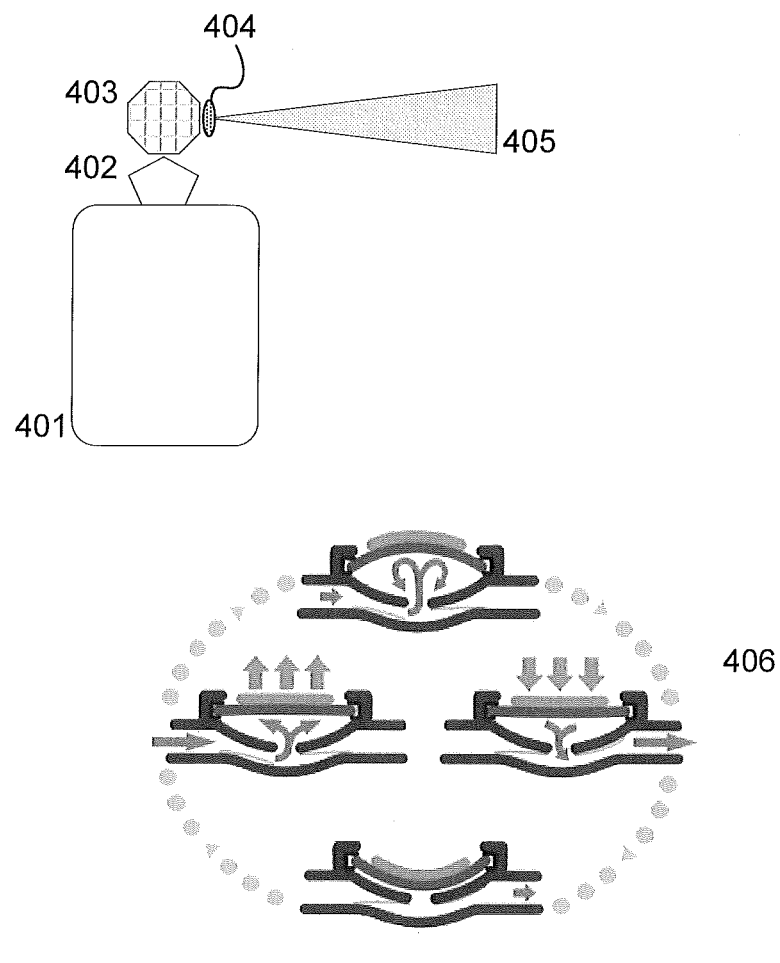
FIG. 4 illustrates an exemplary pump suitable for administering a predetermined dose of a liquid to an eye.

Referring now to FIG. 4, an exemplary pumping device for liquid dispensing to an eye is illustrated with a main reservoir 401, a dosing reservoir 402, an electrically controlled pumping mechanism 403, and an eye orifice nozzle 404. When the pumping mechanism 403 is activated it draws from one or both of the main reservoir 401 and the dosing reservoir 402 and pumps a liquid spray 405 or liquid mist into an eye proximate to the eye orifice nozzle 404.

The main reservoir 401 can contain a liquid to be dispensed into the eye. The liquid can include, for example, a solution useful for treating dryness or other condition in the eye, a medicament, a nutrient or other substance efficacious to the eye.

In some embodiments, a single dose reservoir 402 is included. Other embodiments work directly from the main reservoir 401. The single dose reservoir 402 is in liquid communication with the main reservoir 401 and can be filled with an amount generally equal to a single dose of liquid to be administered to the eye.

The pump draws from one or both of the single dose reservoir 402 and the main reservoir 401. The pump can include a piezo electric pump, a diaphragm type pump, a positive displacement type pump or other device capable of pumping specific amounts of a liquid into the eye. In some preferred embodiments, a piezo electric type pump generally used to administer specific amounts of liquid on a regular basis, such as for example, a piezo electric pump used to pump pharmaceuticals into a an intravenous feed, may be adapted to pump a liquid from one or both of the reservoirs 401-402, through the eye nozzle orifice. Typically, a pharmacy administering pump would need to be adapted to pump with a shorter duration and higher pressure action in order to provide the pulsatile delivery required to administer a liquid to an eye. This is a change from the constant low speed, but tightly controlled amounts fed into an intravenous feed. Some specific examples can include the MP5 and MP6 offered by Bartels Mikrotechnik GmbH. A functional diagram of how a micropump may operate is also included 406.
Specifications May Include, for Example:
Pump type piezoelectric diaphragm pump
Number of actuators 2
Dimensions without connectors 30×15×3.8 mm$^3$
Weight 2 g
Fluidic connectors tube clip (outer diameter 1.6 mm, length 3.5 mm)
Electric connector flex connector/Molex FCC
1:25 mm pitch
Power consumption<200 mW
Self-priming yes 2
Pumping media liquids, gases and mixtures
Operating temperature 0-70° C. 3
Life time 5000 h 3
IP code IP33 4
Materials in contact with media polyphenylene sulphone (PPSU)
Suitable evaluation controller mp-x and mp6-OEM
Typical values of flow and back pressure for selected media (values defined with mp-x: 250 V, SRS):
Gases Max. flow on request
Max. back pressure on request
Liquids Water Max. flow 6 ml/min+/−15% (100 Hz)
Max. back pressure 550 mbar+/−15% (100 Hz)
Additional Examples of Pump Specifications May Include:
Pump type piezoelectric diaphragm pump
Number of actuators 1
Dimensions without connectors 14×14×3.5 mm$^3$
Weight 0.8 g
Fluidic connectors tube clip (outer diameter 2 mm, length 3 mm)
Electric connector flex connector/phone jack
Power consumption<200 mW
Self-priming yes 2
Pumping media liquids or gases
Operating temperature 0-70° C.
Life time 5000 h 3
IP code IP44
Materials in contact with media polyphenylene sulphone (PPSU),
polyimide (PI), nitrile butadiene
rubber (NBR)
Suitable evaluation controller mp-x and mp5-a
Typical values of flow and back pressure for selected media (values defined with mp-x: 250 V, SRS):
Gases Max. flow 15 ml/min (300 Hz)
Linear range 0-5 ml/min @ 0-50 Hz
Max. back pressure 30 mbar (300 Hz)
Liquids Water Max. flow 5 ml/min (100 Hz)
Linear range 0-3 ml/min @ 0-30 Hz
Max. back pressure 250 mbar (100 Hz)
Repeatability
(30 Hz, 250 V, SRS)
<12%
Viscosity<~120 mPas
1 Typical values. Values can vary under application conditions. Content is subject to changes without notice. 2 Conditions: suction pressure<10 mbar, DI water, settings mp-x: 100 Hz, 250 V, SRS, the max. flow rate can be reached by manual priming. 3 Conditions: DI water, room temperature, settings mp-x: 100 Hz, 250 V, SRS.

In some preferred embodiments, the pump will provide enough pressure to spray into an eye from a distance of about 15 millimeters (mm). Distances may therefore be between about 5 mm and 45 mm. In addition, an amount of spray should be controllable within about 5 micro liters of accuracy in amounts of between 3 and 30 micro liters, and preferably about 15 micro liters.

According to some embodiments of the present invention, the detector is placed in logical communication with the automated pump 403 capable of dispensing a predetermined amount of a liquid through the eye orifice nozzle and into the eye.

Figure 5:
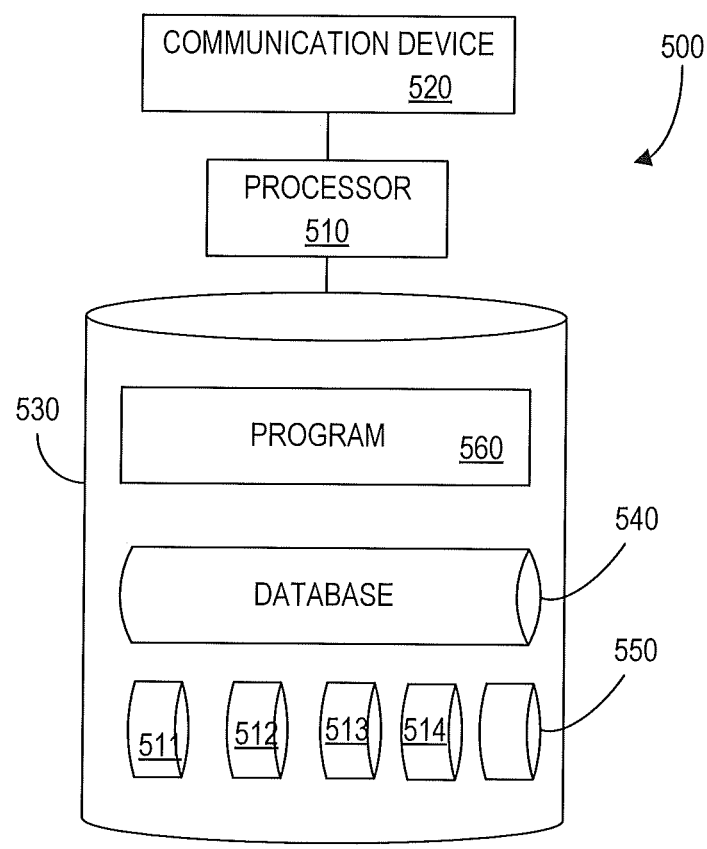
FIG. 5 illustrates a controller that may be used to implement some embodiments of the present invention.

Referring now to FIG. 5 a microcontroller 500 is illustrated that may be used in some embodiments of the present invention. The microcontroller 500 includes a processor 510, and one or more processor components and/or support function circuitry 511-514 such as a crystal oscillator, timers, watchdog timer, serial and analog I/O etc.; program memory in the form of NOR flash or OTP ROM is also often included, as well as some amount of RAM.

The microcontroller 500 may also include a communication device 520. In some embodiments, a microcontroller 500 can be used to receive a logical indication that an eye is in a first state or a second state and transmit energy to a liquid dispenser at a time appropriate to dispense a liquid or mist into the eye, based upon the transition from a first state to a second state. Other logic may also be programmed into the microcontroller and provide for flexibility of function. By way of non-limiting example, such functionality may include monitoring how much fluid is currently stored in one or both of the main reservoir and the dose reservoir; duration of pump actuation which correlates into an amount of liquid administered to the eye, which reservoir is being drawn from; periodic timing of liquid disbursement; duration of liquid disbursement and almost any other functionality related to the operation of the pump.

The one or more processors can be coupled to a communication device 520 configured to communicate energy via a communication channel. The communication device may be used to electronically control, for example, one or more of: timing of liquid dispensing; an amount of liquid dispensed; a duration of a dispensing motion; tracking a number of dispensing actions; tracking chronological dispensing patterns or other actions related to the dispensing.

The processor 510 is also in communication with a storage device 530. The storage device 530 may comprise any appropriate information storage device, including for example: semiconductor memory devices such as Random Access Memory (RAM) devices and Read Only Memory (ROM) devices.

The storage device 530 can store a program 560 for controlling the processor 510. The processor 510 performs instructions of the program 560, and thereby operates in accordance with the present invention. For example, the processor 510 may receive information descriptive of liquid to be dispensed, dispensing amounts, dispensing patterns, and the like.

In addition, the present invention may include an Energy Source 550, such as an electrochemical cell or battery as the storage means for the energy and in some embodiments, encapsulation, and isolation of the materials comprising the Energy Source from an environment into which an ophthalmic pump is placed. The Energy Source 550 can provide power to activate the microcontroller. In some embodiments, power consumption of a microcontroller while sleeping (CPU clock and most peripherals off) may be just nanowatts.

CONCLUSION

The present invention, as described above and as further defined by the claims below, provides apparatus and methods of providing a reservoir for dispensing a small volumes of liquid in precise volumes without Pull Back, thereby preventing contamination of the liquid.

The invention claimed is:

1. A liquid dispensing device for dispensing a precise quantity of a liquid into an ophthalmic environment of an individual, the liquid dispensing device comprising:
   a self-collapsible medical grade liquid reservoir comprising a rigid base portion attached and sealed to a highly sensitive flexible foil lid portion having a thickness in the range of 0.03 millimeters to 0.4 millimeters, to form a sealed cavity between the rigid base and the flexible foil lid,
   wherein the attachment of the rigid base portion to the highly sensitive flexible foil lid portion provides for an increased sensitivity of the highly sensitive flexible foil lid portion, and the cavity formed by the rigid base portion and the highly sensitive flexible foil lid portion is capable of containing a volume of 1 milliliter to 20 milliliters of the liquid, and the highly sensitive flexible foil lid portion is configured to respond to a pressure differential created by dispensing a liquid volume as small as 0.5 microliters;
   a pump;
   a dispensing tip positionable towards an eye of the individual to dispense the liquid onto a surface of an eye or into an area protected by an eyelid; and
   a liquid fluid path providing a fluid connection between the self-collapsible medical grade liquid reservoir, the pump and the dispensing tip.

2. The liquid dispensing device of claim 1, additionally comprising one or more ports in liquid communication with the self-collapsible medical grade liquid reservoir.

3. The liquid dispensing device of claim 2, wherein the liquid fluid path comprises at least one tube in liquid communication with at least one of the one or more ports of the self-collapsible medical grade liquid reservoir.

4. The liquid dispensing device of claim 1, wherein the highly sensitive flexible foil lid portion is adhered to the rigid base portion using a clamping frame.

5. The liquid dispensing device of claim 1, wherein the highly sensitive flexible foil lid portion is adhered to the rigid base portion using a medical grade epoxy.

6. The liquid dispensing device of claim 1, wherein the highly sensitive flexible foil lid portion is adhered to the rigid base portion using heat staking.

7. The liquid dispensing device of claim 1, wherein the liquid fluid path further comprises a valve.

8. The liquid dispensing device of claim 7, wherein the valve is a check valve.

9. The liquid dispensing device of claim 1, wherein the pump is an automated electrical pump.

10. The liquid dispensing device of claim 9, wherein the automated electric pump is controlled by and in logical communication with a microprocessor.

11. The liquid dispensing device of claim 1, wherein the self-collapsible medical grade liquid reservoir, the pump, the dispensing tip and the liquid fluid path are aseptic.

12. The liquid dispensing device of claim 10, additionally comprising an energy source adapted to energize the microprocessor and the automated electric pump.

13. The liquid dispensing device of claim 1, wherein the highly sensitive flexible foil portion is configured to respond to the pressure differential by collapsing.

14. The liquid dispensing device of claim 3, wherein the at least one tube extends outwardly from the rigid base portion of the self-collapsible medical grade liquid reservoir.

15. The liquid dispensing device of claim 1, wherein the highly sensitive flexible foil lid portion includes polyethylene copolymer film.

16. The liquid dispensing device of claim 10, additionally comprising a dispensing head directly connected to the liquid fluid path.

17. The liquid dispensing device of claim 16, wherein the dispensing head is capable of jet dispensing with use of the microprocessor and the automated electric pump.

18. The liquid dispensing device of claim 10, additionally comprising an internal shell comprising the microprocessor, the automated electric pump, and at least a portion of the liquid fluid path.

19. The liquid dispensing device of claim 18, wherein the internal shell and the self-collapsible medical grade liquid reservoir share a point of connection, wherein the point of connection is adapted for removal and replacement of the self-collapsible medical grade liquid reservoir.

20. The liquid dispensing device of claim 19, additionally comprising an access point providing access to the self-collapsible medical grade liquid reservoir.

21. The liquid dispensing device of claim 19, additionally comprising an adaptor connecting the internal shell to the self-collapsible medical grade liquid reservoir.

22. The liquid dispensing device of claim 19, wherein the automated electric pump is one of a peristaltic pump, a piezoelectric pump, a diaphragm type pump, or a positive displacement type pump.

\* \* \* \* \*